US008834386B2

(12) United States Patent
Derkx (10) Patent No.: US 8,834,386 B2
(45) Date of Patent: Sep. 16, 2014

(54) NOISE REDUCTION OF BREATHING SIGNALS

(75) Inventor: Rene Martinus Maria Derkx, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 264 days.

(21) Appl. No.: 13/382,304

(22) PCT Filed: Jul. 2, 2010

(86) PCT No.: PCT/IB2010/053042
§ 371 (c)(1),
(2), (4) Date: Jan. 5, 2012

(87) PCT Pub. No.: WO2011/004299
PCT Pub. Date: Jan. 13, 2011

(65) Prior Publication Data
US 2012/0157870 A1    Jun. 21, 2012

(30) Foreign Application Priority Data

Jul. 7, 2009 (EP) .................................... 09164723

(51) Int. Cl.
*A61B 5/08* (2006.01)
*A61B 7/00* (2006.01)

(52) U.S. Cl.
CPC ............... *A61B 7/003* (2013.01); *A61B 5/0803* (2013.01)
USPC ......................................... 600/529; 702/191

(58) Field of Classification Search
USPC ................................. 600/529; 702/191, 195
See application file for complete search history.

(56) References Cited

U.S. PATENT DOCUMENTS

| 5,797,852 A | 8/1998 | Karakasoglu | |
|---|---|---|---|
| 6,175,602 B1 * | 1/2001 | Gustafsson et al. | 375/346 |
| 6,290,654 B1 | 9/2001 | Karakasoglu | |
| 7,460,901 B2 * | 12/2008 | Kettunen et al. | 600/513 |
| 2006/0200344 A1 * | 9/2006 | Kosek et al. | 704/226 |
| 2009/0024046 A1 | 1/2009 | Gurman | |

FOREIGN PATENT DOCUMENTS

| EP | 1810618 A1 | 7/2007 |
|---|---|---|
| WO | 2008098943 A2 | 8/2008 |

OTHER PUBLICATIONS

Lin et al "Wheeze Recognition based on 2D Bilateral Filtering of Spectrogram" Biomedical Engineering—Applications Basis & Communications, vol. 18, No. 3, 2006, pp. 128-137.
Ding et al "2D Spectrogram Filter for Single Channel Speech Enhancement" Proceedings of the 7th WSEAS International Conference on Signal, Speech and Image Processing, 2007, pp. 89-93.
Nishida, Yoshifumi et al "Monitoring of Breath Sound under Daily Environment by Ceiling Dome Microphone" Proceedings of 2000 IEEE International Conference on System, Man and Cybernetics, 2000, pp. 1822-1829.

* cited by examiner

*Primary Examiner* — Michael D'Angelo
*Assistant Examiner* — Etsub Berhanu
(74) *Attorney, Agent, or Firm* — Larry Liberchuk (57) ABSTRACT

The invention relates to a system for and a method of processing breathing signals. A noise reduction operation is performed on a spectral breathing signal (18) to compute an output spectral signal (38), said noise reduction operation using spectral subtraction; and a two-dimensional frequency and time filtering (32) of a gain function (30) used in the spectral subtraction of the noise reduction operation performing step is performed, for example, a two-dimensional frequency and time median filtering of the gain function. For example, said spectral breathing signal is computed based on a breathing signal.

12 Claims, 4 Drawing Sheets

NOISE REDUCTION OF BREATHING SIGNALS

The invention relates to the field of processing breathing signals, in particular acoustic breathing signals, and more specifically to a method of processing breathing signals and to a system for processing breathing signals.

BACKGROUND OF THE INVENTION

The breathing signal or respiratory signal and the respiratory rate are fundamental vital signs. The respiratory rate may for example be obtained from measured respiratory waveforms. For example, respiratory waveform signals are generated through sensor electrodes externally attached to the person whose respiration is to be measured. Respiratory waveforms may also be derived from electrocardiogram (ECG) waveforms.

U.S. Pat. No. 6,290,654 B1 discloses an apparatus for detecting a breath pattern of a breathing patient. An aerial microphone is utilized to sense breathing or snoring sounds. Audible sound signals from the body of the patient are converted by the microphone and a further tracheal microphone located on the patient's neck to electrical signals, which are supplied to A/D-converters. The output from the respective A/D converter is supplied to an active noise cancellation unit for suppressing background noise using an adaptive linear filter consisting of a set of delay line elements, each of which is represented by one sampling period of delay, and a corresponding set of adjustable coefficients. The output of the adaptive linear filter is subtracted from the sensor output. The resulting output is used to adjust the tap weights in the adaptive linear filter in order to minimize the mean-square value of the overall output. The signal noise from the trachea microphone is treated in a similar manner as the signal noise from the aerial microphone. The signals are band-pass filtered and supplied to an estimated volume of airflow waveform generation unit.

SUMMARY OF THE INVENTION

Measurements, which require the placement of microphones or sensor electrodes attached to a person, are obtrusive in nature and inconvenient for the person. This is specifically important when breathing signals of a sleeping person are to be processed.

Therefore, it would be desirable to be able to process breathing signals captured by a microphone positioned distant from the breathing person.

For example, when recording breathing signals by a microphone, the microphone may be placed in the vicinity of the breathing person, e.g., 50 cm away from the breathing person. However, as the acoustic energy resulting from the breathing is generally very weak, the signal-to-noise ratio, i.e. the ratio between the respiratory signal and the noise, can be very low, making it difficult to extract a relevant respiratory parameter such as the respiratory rate from the signal.

It would be desirable to be able to perform a noise reduction operation of a new kind in order to facilitate determining a respiratory parameter when capturing an acoustic breathing signal at a distance from the sleeping person.

It has been found that most microphones, which have an amplifier built inside the microphone, show a sensor noise that exhibits a low-pass character due to 1/f-noise of the amplifier. Some microphones, like MEMS (micro-electromechanical system) sensors have a signal to noise ratio (SNR), i.e. a signal to sensor-noise ratio, of approximately 60 dB. Other, superior microphones may have an SNR range of 70 to 80 dB.

It would be desirable to provide a method or system for processing breathing signals, which method or system facilitates reducing sensor-noise from a microphone.

To better address one or more of these concerns, in a first aspect of the invention, a method of processing breathing signals is provided, the method comprising:
performing a noise reduction operation on a spectral breathing signal to compute an output spectral signal, said noise reduction operation using spectral subtraction; and
performing a two-dimensional frequency and time filtering of a gain function used in the spectral subtraction of the noise reduction operation performing step.

For example, the noise reduction operation comprises said step of performing a two-dimensional filtering of the gain function.

For example, the method further comprises:
computing said spectral breathing signal based on a breathing signal, e.g. based on a breathing signal in time domain.

For example, the breathing signal is an acoustic breathing signal. For example, the breathing signal is a signal captured by a microphone.

For example, the step of computing the spectral breathing signal comprises a fast Fourier transformation (FFT).

The term "noise reduction operation" is to be understood to mean an operation that is suitable to reduce noise, e.g. sensor noise, contained in a signal represented by the spectral breathing signal.

The term "filtering" is to be understood as comprising averaging, median filtering and other filtering algorithms.

In the noise reduction operation using spectral subtraction, a gain function is used as will be described in further detail further below.

In general, the breathing increases and decreases very slowly over time. Further, the frequency-content of a breathing signal does not show significant peaks and valleys like, e.g., in formants of speech signals. It has been found that the spectral characteristics of breathing sounds show relevant information up to approximately 2 kHz. Since there are large areas in the time-frequency characteristics of a breathing signal that do not show huge peaks and valleys, a two-dimensional frequency and time filtering of the gain function may advantageously be applied. Thereby, noise reduction can be improved while avoiding an unacceptable distortion of the breathing signal.

For example, said two-dimensional frequency and time filtering of the gain function is a two-dimensional frequency and time averaging/median filtering, i.e., an averaging or a median filtering. In general, filter algorithms like averaging or median filtering are especially suitable for eliminating outliers.

In one embodiment, the two-dimensional frequency and time filtering of the gain function is a two-dimensional frequency and time median filtering. A median filtering is especially advantageous in that it allows eliminating outliers by replacing the outliers by other values without smoothing the relevant signal portions. Thus, the quality of the noise reduction operation is improved.

For example, the method further comprises providing an output signal based on converting the output spectral signal to the time domain. This may be advantageous for computing a respiratory parameter. For example, converting the output spectral signal to the time domain may comprise an inverse fast Fourier transformation (IFFT).

For example, the method comprises computing at least one respiratory parameter based on the output spectral signal. An important respiratory parameter is, for example, the respiratory rate. For example, said at least one respiratory parameter is computed based on said output signal obtained by converting the output spectral signal to the time domain. For example, the at least one respiratory parameter is a sleep quality parameter. Thus, sleep quality may be determined. For example, the sleep quality of a sleeping person may be determined or estimated, and a control signal may be provided based on a sleep quality estimation. For example, the control signal may be a signal for controlling or influencing external factors of a sleeping environment, such as a temperature, a lighting, etc. For example the one or more control signals may be chosen for improving or enhancing the sleep of a sleeping person. Another possibility is to provide a control signal for waking up a person, when the sleep quality of the person is estimated as being too low, for example being below a sleep quality threshold value.

In one embodiment, the gain function that is used in the spectral subtraction is computed based on estimated noise and a magnitude spectral signal, which is computed based on the spectral breathing signal. For example, computing the gain function may comprise dividing an estimated noise spectrum by the absolute value spectral signal. However, instead of the absolute value spectral signal, for example, also the square absolute value may be used, i.e. a power spectral signal. Thus, in this case, the gain function is computed based on the estimated noise and the square of the magnitude spectral signal.

For example, the noise reduction operation comprises the steps of:
    computing a magnitude spectral signal based on the spectral breathing signal;
    computing a gain function based on estimated noise and the magnitude spectral signal;
    performing a two-dimensional frequency and time filtering of the gain function; and
    computing an output spectral signal by multiplying the spectral breathing signal with the filtered gain function.

That is, the noise reduction operation comprises the above mentioned step of performing a two-dimensional filtering of the gain function. Thus, an efficient noise reduction operation is achieved.

For example, the noise reduction operation comprises estimating noise, said estimating of noise comprising an averaging operation based on several successive blocks of a magnitude spectral signal, said magnitude spectral signal being computed based on the spectral breathing signal. For example, the magnitude spectral signal may be averaged over several successive blocks. Alternatively, for example, the square of the magnitude spectral signal, i.e. a power spectral signal, may be averaged. Thus, an a priori knowledge that the noise is stationary is used. This is particular advantageous, for example, in a situation where the noise is mainly determined by the sensor noise of a microphone, because such sensor noise is highly stationary. For example, the averaging operation is performed for each frequency bin, i.e. each element of the set of discrete frequencies on which the spectral signal function is defined, e.g. in particular the frequency bins of the FFT. For example, said number of successive blocks corresponds to a period of time of at least 1 second, preferably at least 3 seconds, in particular at least 10 seconds. Thus, a high quality of the noise floor estimation may be achieved.

For example, said two-dimensional frequency and time filtering of the gain function is performed with a filter kernel that corresponds to a time span of at least 0.05 seconds, more preferably at least 0.1 seconds or, even more preferably, at least 0.25 seconds.

For example, said two-dimensional frequency and time filtering of the gain function is performed with a filter kernel that corresponds to at least 3 successive blocks of the magnitude spectral signal used in the noise reduction operation, the block size being, for example, 512 samples. More preferably, the number of blocks is at least 5 or, even more preferably, at least 7. Thus, noise reduction may be improved.

For example, said two-dimensional frequency and time filtering of the gain function is performed with a filter kernel corresponding to a frequency span of at least 40 Hz, more preferably at least 75 Hz, or, even more preferably, at least 100 Hz. For example, the filter kernel may correspond to a frequency span of at least 250 Hz. For example, said two-dimensional frequency and time filtering of the gain function is performed with a filter kernel corresponding to at least 3 frequency bins, more preferably at least 5 frequency bins or, even more preferably, at least 7 frequency bins. Thus, sensor noise may be efficiently removed.

For example, the method comprises sampling the breathing signal at a sampling frequency of at least 4 kHz, preferably at least 8 kHz. The use of such comparatively high sampling frequency is advantageous in that the spectral characteristics of breathing sounds show relevant information up to 2 kHz. Therefore, noise reduction may be improved.

For example, the method may comprise down-sampling an output signal that is computed based on the output spectral signal. Using a higher sampling frequency for the noise reduction operation than what would be necessary for computing a respiratory parameter allows an improved noise reduction. For example, the sampling frequency may be at least 8 kHz. Furthermore, using a high sampling frequency allows the two-dimensional filtering of the gain function in frequency and time to be performed without distorting the breathing sounds.

In one embodiment, the method further comprises adapting a filter kernel width and/or a filter kernel length of a filter kernel used in said two-dimensional frequency and time filtering of the gain function; said adapting being based on a ratio between signal energy contained in a first time-frequency area and noise energy, e.g. energy of musical tones, contained in a second time-frequency area of a signal that is obtained based on two-dimensional frequency and time filtering of the gain function. Such signals are, for example, the filtered gain function, the spectral output function, or the output function, which all depend on the filtered gain function. For example, said signal may be a filtered gain function obtained by two-dimensional frequency and time filtering of the gain function. For example, the first time-frequency area is composed of a first frequency range and a first time range, and the second time-frequency area is composed of a second frequency range and a second time range. For example, the first frequency range is a lower frequency range, and the second frequency range is a higher frequency range. The filter kernel width corresponds to a frequency-span, and the filter kernel length corresponds to a time-span of the filter kernel. Preferably, the first and second time-frequency areas are chosen such that the energy of the wanted signal, i.e. a breathing sound, substantially contributes to the energy contained in the first time-frequency area. Thus, energy contained in the neighborhood but outside the first time-frequency area, and, in particular, energy contained in the appropriately chosen second time-frequency area, may be attributed to noise, such as the musical tones.

The terms "signal energy" and "noise energy" refer to the integrated square of the absolute value of the signal amplitude, and may be computed in the time domain or frequency domain. That is, the term "noise energy" is to be understood as meaning signal energy assumed to be attributable to noise.

For example, said adapting comprises optimizing a ratio between the signal energy contained in a first time-frequency area and the noise energy contained in a second time-frequency area of said function.

For example, the first time range may be selected such that it corresponds to or includes a (locally) maximum signal energy of said signal.

For example, said first and second time ranges may be without overlap. For example, said first and second time ranges may be consecutive time ranges. For example, the second time range may precede the first time range.

For example, the filter kernel width and/or filter kernel length is adapted stepwise, e.g. by a fixed number of frequency bins or a fixed number of time-blocks.

For example, said signal is obtained based on two-dimensional frequency and time filtering of the gain function, said filtering being performed with a test filter kernel, a width and/or a length of which are different from a width respectively length of the filter kernel currently used in the step of performing a filtering of the gain function.

Adapting the filter kernel width and/or filter kernel length is advantageous for the following reasons.

The characteristic time-frequency patterns of breathing signals can vary over time and over specific persons. For example, people may have in- and exhales where most of the breathing energy is concentrated in a specific time span, while for other people the breathing energy may spread over a longer time span. Similarly, the frequency characteristics can also vary over different people. Besides the differences over persons, there can also be differences in the time-frequency characteristics of the breathing signal of a single person over time. For example, when the person has a cold, generally the breathing process occurs through the mouth instead of the nose, and the time-frequency characteristics are likely to be altered.

While musical tones caused by the spectral subtraction may be minimized or removed by choosing a large enough kernel size, a too large kernel size may lead to distortion of the breathing sounds, such as smearing out in the frequency spectrum and/or in time. Thus, adapting the filter kernel width and/or filter kernel length may improve the noise reduction while minimizing the distortion of breathing sounds.

In a further aspect of the invention, there is provided a system for processing breathing signals, comprising:

a noise reduction unit for computing an output spectral signal by performing a noise reduction operation on a spectral breathing signal, wherein the noise reduction operation uses spectral subtraction; and a filter unit or filter for performing a two-dimensional frequency and time filtering of a gain function used in the spectral subtraction.

For example, the system may be adapted for performing the method of processing breathing signals as described above.

For example, the system further comprises:

a spectral analyzing unit or spectrum analyzer for computing said spectral breathing signal based on a breathing signal, i.e. a breathing signal in the time domain.

For example, the breathing signal is input to the spectrum analyzing unit. For example, an output of the spectrum analyzing unit comprising the spectral breathing signal is input to the noise reduction unit.

For example, the output spectral signal is output by the noise reduction unit. For example, the noise reduction unit comprises a filter unit. For example, the filter unit is a median filtering unit for performing a two-dimensional frequency and time median filtering of the gain function. For example, the spectrum analyzing unit, the noise reduction unit and/or the filter unit are parts of a spectral subtraction unit of the system for filtering the breathing signal.

For example, the system further comprises a synthesizing unit for computing an output signal based on converting the output spectral signal to the time domain.

For example, an output of the spectrum analyzing unit is coupled to an input of the noise reduction unit. For example, an output of the noise reduction unit is coupled to an input of the synthesizing unit.

For example, the system further comprises a breathing analyzing unit for computing at least one respiratory parameter based on the output spectral signal. For example, an output of the noise reduction unit or an output of the spectral subtraction unit or an output of the synthesizing unit may be coupled to an input of the breathing analyzing unit.

In one embodiment, the system further comprises a filter adapting unit for adapting a filter kernel width and/or a filter kernel length of a filter kernel used in said two-dimensional frequency and time filtering of the gain function, wherein said adapting is based on a ratio between signal energy contained in a first time-frequency area noise energy contained in a second time-frequency area of a signal that is obtained based on two dimensional frequency and time filtering of the gain function. The filter adapting unit may be arranged for performing the step of adapting a filter kernel width and/or a filter kernel length as described above.

These and other aspects of the invention will be apparent from and illustrated with reference to the embodiments described hereinafter.

DETAILED DESCRIPTION OF EMBODIMENTS

Figure 1:
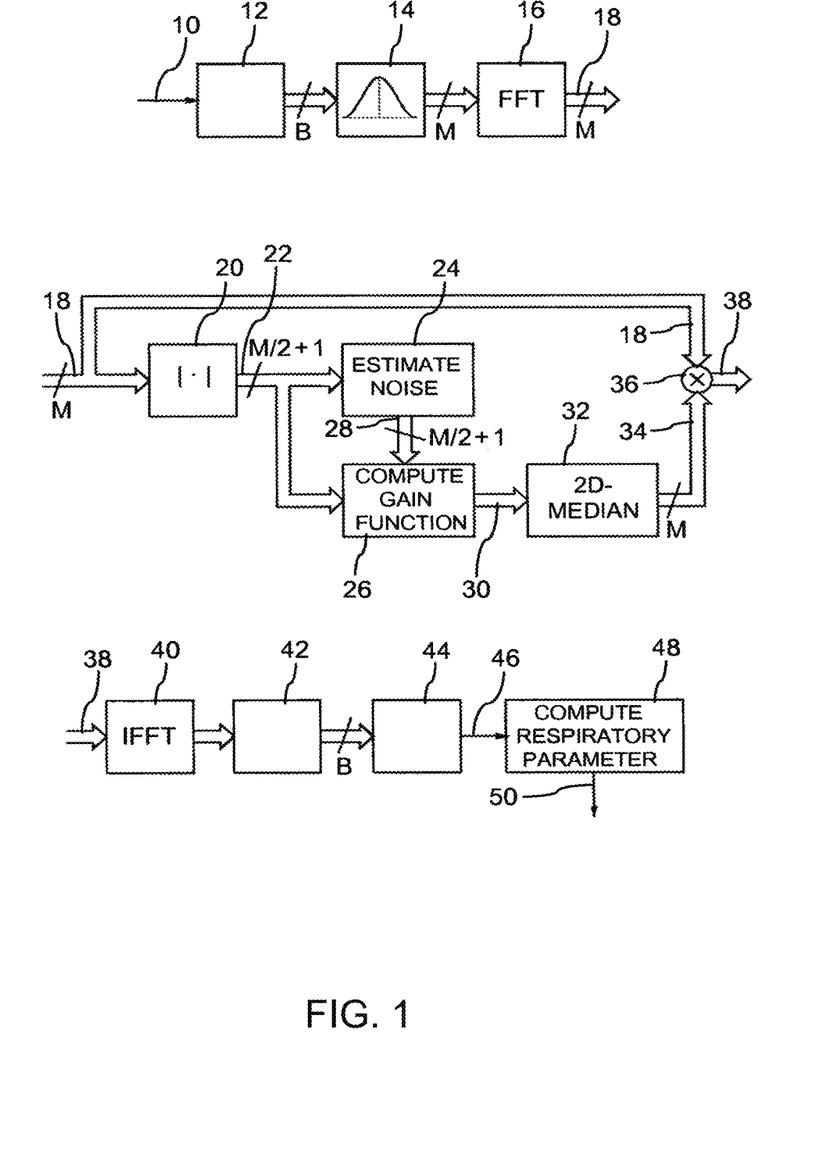
FIG. 1 schematically illustrates a system for processing breathing signals, and the data flow in the system.

FIG. 1 exemplarily shows a system for processing breathing signals. The system and a method of processing breathing signals will be described in the following with reference to FIG. 1.

In FIG. 1, a signal or data flow is schematically illustrated by arrows. A thin lined arrow illustrates a signal in the time domain or, if explicitly mentioned, one or more parameters. Thick, outlined arrows symbolize the flow of data blocks in time domain or data blocks in frequency domain.

A breathing signal 10 captured by a microphone, which is positioned at a distance of e.g. 50 cm from a sleeping person, is sampled and arranged in time-blocks by a sampler or sampling unit 12. For example, the sampling frequency is 8 kHz.

A sampling rate of 8 kHz is sufficient for keeping the relevant information of the breathing sounds in the breathing signal. For example, the signal is converted to consecutive blocks of B samples. For example, B=256.

The output of the sampling unit 12 is coupled to an input of a block concatenating and windowing unit 14, which constructs consecutive time-blocks or blocks of M samples by concatenating samples of a current block with samples from at least one previous block. For example, the samples of the current block are concatenated with the samples of the previous block to M samples, wherein M=2B. For example, M=512.

For example, the M samples of a block are windowed by a Hann window, which is also known as a raised cosine window.

The output of the unit 14 is coupled to an input of a spectrum analyzing unit 16. For example, the unit 16 converts the block of M samples to the frequency domain using an FFT operation. Thus, the unit 16 outputs a spectral breathing signal 18 in the form of consecutive, overlapping time-blocks of a complex spectrum that has M frequency-bins. The output of the unit 16 is coupled to an input of a magnitude spectrum computing unit 20. The unit 20 converts the complex frequency spectrum of the spectral signal 18 to a magnitude spectral signal 22 having M/2+1 frequency bins. For example, M/2+1=257 at a frequency resolution of 15.625 Hz.

The output of the unit 20 is coupled to an input of a noise estimation unit 24 and to an input of a gain function computing unit 26.

The noise estimation unit 24 estimates a spectral noise floor and outputs a magnitude noise spectrum signal 28 to the gain function computing unit 26. Thus, the output of the unit 24 is coupled to a further input of the unit 26. For example, the noise is estimated by averaging over several successive time blocks of the magnitude spectral signal 22. For example, the number of blocks of the signal 22 may correspond to a time period of 10 seconds or more.

The unit 26 computes a gain function 30 based on the magnitude spectral signal 22 and the estimated magnitude noise spectral signal 28. For example, the gain function 30 has the form of consecutive blocks of a spectrum having spectral values between 0 and 1 and a block size of M/2+1.

The calculation of a gain function for spectral subtraction of noise is known as such in the art of speech enhancement, for example. In general, the gain function is computed such that the spectral subtraction of noise may be performed by multiplying the spectral signal 18 by the gain function 30 in the frequency domain. For example, the spectrum or gain function 30 may be computed as $G_n = \max(1 - W_n/|X|, \lambda)$, wherein X is the spectral breathing signal 18, W is the estimated noise spectral signal, and $n=0, \ldots, M/2+1$. Here, $\lambda$ is the so-called spectral floor to limit the amount of noise reduction. If $\lambda=0$, a maximum amount of noise reduction is obtained.

The spectrum or gain function 30 output by the unit 26 is input to a filtering unit 32, for example a 2D median filtering unit. The filtering unit 32, for example, performs a two-dimensional frequency and time median filtering of the gain function or spectrum 30. For example, the filtering unit 32 has a median filtering kernel having a width of 7 frequency bins and a length of 7 time blocks. In the median filtering, an extension from M/2+1 frequency bins to M frequency bins is performed by mirroring of the frequency spectrum. The filtering unit 32 outputs a filtered gain function 34.

The output of the unit 32 and of the unit 16 are coupled to inputs of a spectral multiplying unit 36 that multiplies the spectral signal 18 and the filtered gain function 34, thereby performing spectral subtraction of the estimated noise. Thereby, an output spectral signal 38 is created.

The output of the unit 36 is coupled to an input of a synthesizing unit 40 that converts the output spectral signal 38 to the time domain, for example by performing an IFFT.

Thus, the units 20, 24, 26, 32 and 36 form a noise reduction unit for performing a noise reduction operation on the spectral signal 18, thereby computing an output spectral signal 38.

The output of the unit 40 is coupled to an input of a block overlap and add unit 42 that computes blocks of B samples based on the addition of overlapping parts of the blocks of M samples received from unit 40. For example, said blocks of B samples are non-overlapping, consecutive blocks. The blocks output by the unit 42 are converted by a converter unit 44 into a sequence of consecutive samples forming an output signal 46. For example, the converter unit 44 performs a down-sampling. Thus, the output signal 46 may have a sampling frequency that is lower than the sample frequency of the sampling unit 12.

For example, the output of the converter unit 44 is input to a breathing signal evaluation unit 48 that computes at least one respiratory parameter 50 based on the output signal 46. The respiratory parameter, for example, may be the respiratory rate. For example, the breathing signal evaluation unit 48 may compute the respiration rate from the output signal 46 in a manner known as such in the art.

For example, the system for processing breathing signals may comprise a processor for executing a computer program adapted for performing the method described above. For example, the processor and/or the computer program may comprise and/or form one or more of the above described units, such as units 12, 14, 16, 20, 24, 26, 28, 32, 36, 40, 42, 44 and/or 48. For example, the processor and/or the computer program may be a part of a computer adapted for performing the method described above.

Figure 2A:
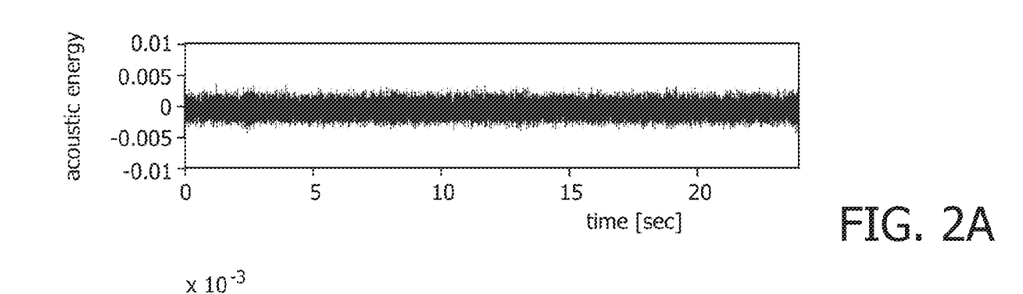
FIG. 2 shows diagrams illustrating the acoustic energy of a breathing signal, of the output signal of a comparative example and of the output signal of the system of FIG. 1.
Figure 2B:
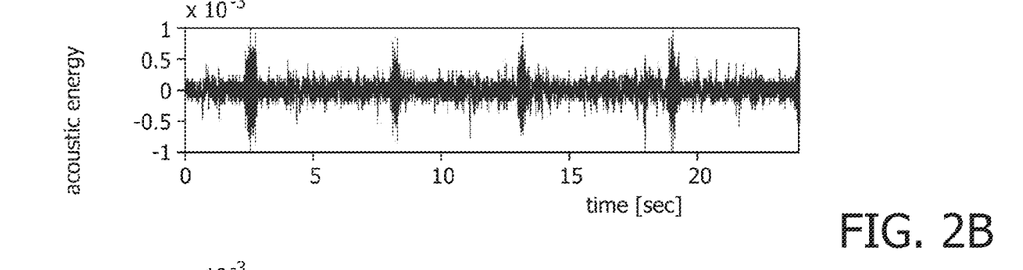
Figure 2C:
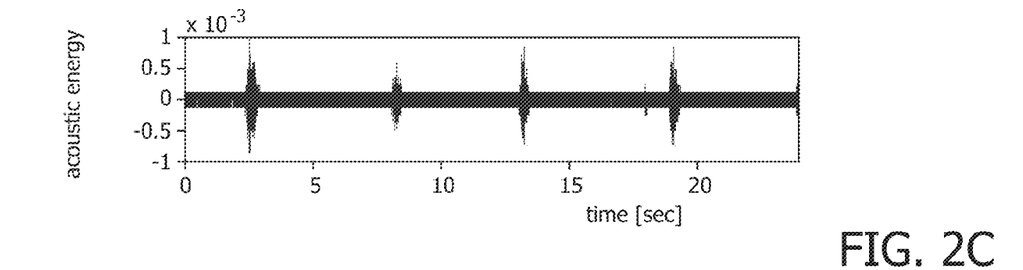

FIG. 2 shows a diagram (A) representing the acoustic energy of a signal over time. The acoustic energy is shown in arbitrary units that refer to the signal values output by the sampling unit 12 of the system of FIG. 1.

The diagram (A) shows a real life recording of a breathing signal of a breathing person over approximately 24 seconds. The breathing signal was recorded using a microphone that was placed at approximately 50 cm from the breathing person. The sample rate was 8000 Hz, and values of B=256 and M=512 have been used. As can be seen in the diagram, the signal to noise ratio is poor, and the sounds of the respirations are not visible by the eye.

As a comparative example, the diagram (B) shows an output signal obtained from a system as shown in FIG. 1, but without performing the median filtering by the unit 32. Thus, the diagram (B) shows the result of a conventional spectral subtraction of estimated noise. It has been found that the spectral subtraction method gives rise to musical tones in the output signal, which have a highly stochastic character in both time and frequency. Some of these musical tones or outliers are visible in the diagram (B). Such outliers could easily be falsely classified as breathing by a breathing signal evaluation unit or procedure.

The diagram (C) shows the result of processing the breathing signal of diagram (A) with the system of FIG. 1 including the 2D median filtering unit 32. The kernel size of 7 frequency bins times 7 time-blocks has been used to obtain an output signal 46 shown in diagram (C). As can be seen, the musical tones are effectively removed. Thus, classification and extraction of respiratory parameters by the unit 48 can be improved.

Because the breathing increases and decreases very slowly over time, and because the frequency content of the breathing also does not show huge peaks and valleys—like they are e.g. present in vowels of speech—, the median filtering may be performed in two dimensions without unduly distorting the breathing sounds.

Figure 3:
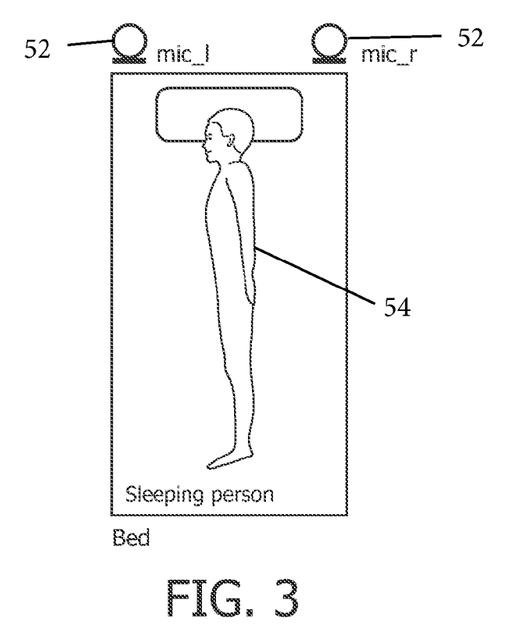
FIG. 3 schematically illustrates a setup for acquiring a breathing signal of a sleeping person.

FIG. 3 schematically shows a possible setup for capturing the breathing signal 10 using one or more microphones 52 placed in the vicinity of a sleeping person 54. For example, two microphones 52 are placed at front corners of a bed. Using two microphones at different positions allows accommodating for changes in positions of the sleeping person 54. For example, the method described above may be performed for two breathing signals 10 corresponding to the different microphones 52, and the breathing signal having the higher signal to noise ratio may be selected for computing the at least one respiratory parameter.

Figure 4:
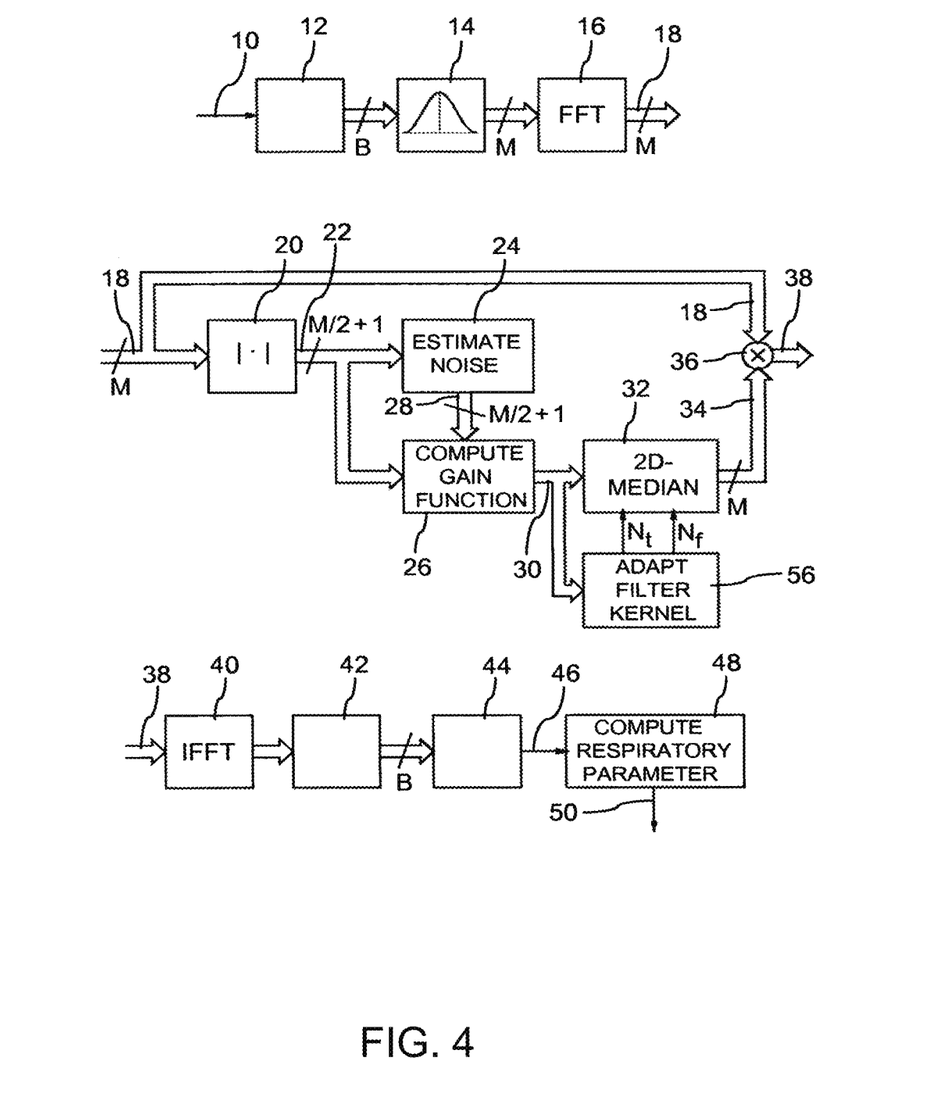
FIG. 4 schematically illustrates a further embodiment of a system for processing breathing signals.

FIG. 4 shows a further embodiment of a system for processing breathing signals that differs from the system of FIG. 1 in that the noise reduction unit further comprises a filter adapting unit 56. The output of the gain function computing unit 26 is coupled to an input of the filter adapting unit 56. The filter adapting unit 56 determines filter parameters, in particular a filter kernel width $N_f$ and a filter kernel length $N_t$ to be used by the filtering unit 32. Parameter outputs of the unit 56 are coupled to parameter inputs of the unit 32.

The kernel size corresponding to a width of a number of frequency bins and a length of a number of time blocks may be interpreted as the model order of the filtering. Thus, $N_f$ is the model order for frequency and $N_t$ is the model order for time.

In order to adapt the filter kernel width $N_f$ and the filter kernel length $N_t$ of the filter kernel used by the unit 32, the unit 56 performs the following computing steps:

The unit 56 determines a first time range for computing the signal energy of a wanted signal, i.e. a breathing sound. For example, a detection moment t is determined at which the signal energy of the gain function reaches a maximum. For example, the first time range is set to [t−0.25, t+0.25], wherein the time values are given in seconds.

For example, a second time range is determined for computing the signal energy of a noise signal. For example, the second time range is set to [t−0.75, t−0.25].

For example, a two-dimensional frequency and time filtering of the gain function is then performed using a test filter kernel having the same kernel size as the one currently used by the unit 32, thereby creating a filtered signal.

For example, the signal energy contained in the first time range and in a first or lower frequency range of e.g. 0 to 2 kHz of the signal is computed, and the signal energy in the second time range and a second or higher frequency range of e.g. 2 to 4 kHz is computed, and the ratio between the two signal energy values is computed.

If this ratio is larger than a certain threshold value, it is assumed that a breathing sound is present. However, if the ratio is less than the threshold value, this indicates that the described musical tones are present in the higher frequency range. Thus, the noise reduction is insufficient.

In the case of insufficient noise reduction, for example, the steps of filtering the gain function with a test filter kernel and determining said ratio may be repeated for one or more test filter kernels of different kernel size, and an optimum kernel size may be selected. The selected kernel filter width $N_f$ and kernel filter length $N_t$ are then output to the filtering units 32.

For example, said ratio may be determined using test filter kernels of kernel sizes or kernel orders $(N_{t\_test}, N_{f\_test})=(N_t−1, N_f), (N_t, N_f−1), (N_t, N_f), (N_t, N_f+1), (N_t+1, N_f)$, wherein $(N_t, N_f)$ is the current kernel size. For example, the kernel order with the optimum ratio may be selected as the new kernel size.

For example, the above described steps of determining first and second time ranges and determining said ratio for the respective time ranges may be repeated for a number of breathes, and the ratio may be averaged over said number of breathes.

For example, the unit 56 may lower the model order for both time and frequency, i.e. reduce the filter kernel width and length by e.g. a value of 1 after a certain time has passed, e.g. every 10 minutes. Thus, a leakage of the model order over time may be applied. This is especially useful if, for determining said ratios by using test filter kernels of different sizes, only test filter kernels having a larger filter kernel width and/or a larger filter kernel length than the filter kernel currently used in the unit 32 are tested.

Adapting the filter kernel width and/or filter kernel length as described above allows determining an optimal filter kernel size for an individual person, breathing condition of the person and/or an acoustic condition. Thus, the computing of the respiratory parameter(s) 50 may be improved.

While the invention has been illustrated and described in detail in the drawings and foregoing description, such illustration and description are to be considered illustrative or exemplary and not restrictive. The invention is not limited to the disclosed embodiments.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. Any reference signs in the claims should not be construed as limiting the scope.

The invention claimed is:

1. A method of processing breathing signals, comprising:
   performing, by a noise reduction unit, a noise reduction operation on a spectral breathing signal to compute an output spectral signal, said noise reduction operation using spectral subtraction; and
   performing, by a filler unit, a two-dimensional frequency and time filtering of a gain function used in the spectral subtraction of the noise reduction operation.

2. The method as claimed in claim 1, wherein said two-dimensional frequency and time filtering of the gain function is a two-dimensional frequency and time averaging or median filtering.

3. The method as claimed in claim 1, further comprising:
   computing, by a spectrum analyzing unit, said spectral breathing signal based on a breathing signal.

4. The method as claimed in claim 1, further comprising:
   computing at least one respiratory parameter based on the output spectral signal.

5. The method as claimed in claim 1, wherein the noise reduction operation comprises:
   computing a magnitude spectral signal based on the spectral breathing signal;
   computing a gain function based on estimated noise and the magnitude spectral signal;
   performing a two-dimensional frequency and time filtering of the gain function; and
   computing an output spectral signal by multiplying the spectral breathing signal (18) with the filtered gain function.

6. The method as claimed in claim 1, wherein said two-dimensional frequency and time filtering of the gain function is performed with a filter kernel that corresponds to a timespan of at least 0.05 seconds.

7. The method as claimed in claim 1, wherein said two-dimensional frequency and time filtering of the gain function is performed with a filter kernel corresponding to a frequency-span of at least 40 Hz.

8. The method as claimed in claim 1, further comprising:

adapting, by a filter adapting unit, a filter kernel width or a filter kernel length of a filter kernel used in said two-dimensional frequency and time filtering of the gain function, wherein said adapting is based on a ratio between signal energy contained in a first time-frequency area and noise energy contained in a second time-frequency area of a signal that is obtained based on two-dimensional frequency and time filtering of the gain function.

9. A system for processing breathing signals, comprising:

a noise reduction unit for computing an output spectral signal by performing a noise reduction operation on a spectral breathing signal, wherein the noise reduction operation uses spectral subtraction; and a filter unit for performing a two-dimensional frequency and time filtering of a gain function used in the spectral subtraction.

10. The system as claimed in claim 9, further comprising:

a spectrum analyzing unit for computing said spectral breathing signal based on a breathing signal.

11. The system as claimed in claim 9, further comprising:

a filter adapting unit for adapting a filter kernel width or a filter kernel length of a filter kernel used in said two-dimensional frequency and time filtering of the gain function, wherein said adapting is based on a ratio between signal energy contained in a first time-frequency area and noise energy contained in a second time-frequency area of a signal that is obtained based on two-dimensional frequency and time filtering of the gain function.

12. A non-transitory computer readable medium including a computer program for performing a method as claimed in claim 1 when the computer program is executed by a computer.

\* \* \* \* \*